United States Patent [19]
Mack et al.

[11] Patent Number: 6,124,472
[45] Date of Patent: Sep. 26, 2000

[54] PROCESS FOR PREPARING 3-PYRROLINE-2-CARBOXYLIC ACID DERIVATIVES

[75] Inventors: Helmut Mack, Ludwigshafen; Thomas Pfeiffer, Böhl-Iggelheim; Werner Seitz, Plankstadt; Thomas Zierke, Böhl-Iggelheim; Friedhelm Balkenhohl, Limburgerhof; Udo Lange, Ludwigshafen, all of Germany

[73] Assignee: BASF Aktiengesellschaft, Ludwigshafen, Germany

[21] Appl. No.: 09/230,321

[22] PCT Filed: Jul. 14, 1997

[86] PCT No.: PCT/EP97/03752

§ 371 Date: Jan. 22, 1999

§ 102(e) Date: Jan. 22, 1999

[87] PCT Pub. No.: WO98/04523

PCT Pub. Date: Feb. 5, 1998

[30] Foreign Application Priority Data

Jul. 26, 1996 [DE] Germany .............. 196 30 082

[51] Int. Cl.[7] .............. C07D 207/18; C07D 207/24
[52] U.S. Cl. .......... 548/530; 548/532; 548/535; 548/565
[58] Field of Search ................. 548/530, 532, 548/535, 565

[56] References Cited

U.S. PATENT DOCUMENTS 4,066,658  1/1978  Felix ............................ 260/326.2
4,501,901  2/1985  Thottathil et al. ............. 548/532

FOREIGN PATENT DOCUMENTS 1 462 258  of 0000  France .
1 462 259  of 0000  France .
1 072 710  8/1964  United Kingdom .
1 120 033  7/1968  United Kingdom .

OTHER PUBLICATIONS

Tet. Ltr. vol. 27, No. 2, –151–154, 1986.
Tet. Ltr. vol. 31, No. 9, 1241–1244, 1990.

Primary Examiner—Joseph McKane
Assistant Examiner—Jane C. Osweckі
Attorney, Agent, or Firm—Keil & Weinkauf

[57] ABSTRACT

3-Pyrroline-2-carboxylic acid derivatives of the formula I

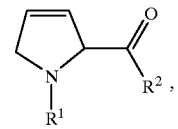

(I)

are prepared by eliminating the sulfonic acid residue, with the aid of a base, from a compound of the formula II

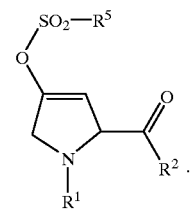

(II)

8 Claims, No Drawings

PROCESS FOR PREPARING 3-PYRROLINE-2-CARBOXYLIC ACID DERIVATIVES

This application is a 371 of PCT/EP97/03752 filed Jul. 14, 1997.

The present invention relates to a novel process for preparing pyrroline-2-carboxylic acid derivatives.

Replacement of proline by 3,4-dehydroproline in biologically active peptides or peptide mimetics rarely causes a loss of activity (A. M. Felix et al. Int. J. Pept. Prot. Res. 10, (1977) 299; C. R. Botos et al. J. Med. Chem. 22, (1979) 926; G. H. Fisher, W. Ryan, FEBS Lett. 107, (1979) 273); on the contrary, in some cases the effect is increased while there is a simultaneous reduction in toxicity (G. H. Fisher, W. Ryan FEBS Lett. 107, (1979) 273; S. Natarajan et al., in Peptide, Structure and Biological Function, E. Gross, J. Meienhofer, Eds., Pierce Chemical Company, 1979, p. 463).

Synthesis of N-protected 3,4-dehydroprolines on the industrial scale by processes disclosed in the literature is very elaborate as shown, for example, by the thermal cis elimination of the S-methylxanthate from hydroxyproline by the Tchugaeff method. The disadvantages of this process are that large amounts of methyl iodide are used, and methyl mercaptan and carbon oxysulfide are produced (J.-R. Dormay et al., Angew. Chem. 92, (1980) 761; Houben-Weil, Methoden der Organischen Chemie, Vol. 5/1b, 126 (1972)).

The reduction of pyrrole-2-carboxylic acid with phosphonium iodide in fuming hydroiodic acid is also problematic because of the use of a large excess of gaseous hydrogen iodide, and of a marked reduction in yield and onset of polymerization in large reactions (J. W. Scott et al., Synth. Commun. 10(7), (1980) 529). On the other hand, elimination of the Boc-protected 4-phenylseleninylproline methyl ester takes place under distinctly milder conditions (J.-R. Dormay, Synthesis 9, (1982) 753. The elimination takes place at room temperature and results in the $\Delta^3$-olefin with high selectivity. Thermal cis eliminations afford considerable amounts of the isomeric $\Delta^4$ olefin. However, elimination of the selenium oxide is also disadvantageous because of the production of toxic selenium-containing residues which require costly disposal precisely in the case of reactions on the pilot-plant scale, and addition of the previously eliminated selenigenic acid to the double bond is disadvantageous especially in the case of pharmaceutical active ingredients in which even tiny amounts of selenium-containing compounds result in toxic properties.

Small amounts of 3-pyrroline have been obtained from N-substituted 3-methylsulfonyloxypyrrolidine (T. Uno et al., J. Heterocycl. Chem. 24, (1987) 1025). Elimination of sulfonates, eg. methylsulfonate, to prepare 3-pyrroline-2-carboxylic acid derivatives has not previously been described.

Said processes disclosed in the literature for preparing 3-pyrroline-2-carboxylic acid derivatives are unsuitable for industrial syntheses.

The present invention relates to a process for preparing 3-pyrroline-2-carboxylic acid derivatives of the formula I

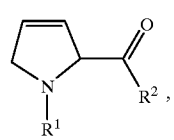

where $R^1$ is H, $C_1$–$C_6$-alkyl, benzyl, benzyl substituted on the phenyl, allyloxycarbonyl, $C_1$–$C_6$-alkyloxycarbonyl, benzyloxycarbonyl where the benzyl residue can be substituted by $OCH_3$ radicals, or $C_1$–$C_4$-alkylcarbonyl or $R^1$ is a residue of an amino acid which is linked via the C terminus and may be alkylated or acylated on the nitrogen, and $R^2$ is OH, $C_1$–$C_4$-alkyloxy, benzyloxy or $NR^3R^4$, where $R^3$ and $R^4$ are, independently of one another, H, $C_1$–$C_4$-alkyl, benzyl, phenyl or pyridyl, it being possible for the aromatic systems in $R^3$ and $R^4$ to be substituted by up to three identical or different substituents selected from the group consisting of methyl, methoxy, hydroxyl, cyano or halogen, which comprises eliminating the sulfonic acid residue with the aid of a base from a sulfonate of the formula II

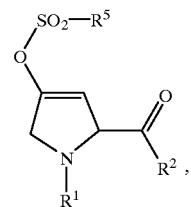

where $R^1$ and $R^2$ have the meanings described above, and $R^5$ is $C_1$–$C_6$-alkyl, benzyl, trifluoromethyl, naphthyl or phenyl which may be unsubstituted or substituted by radicals from the group consisting of methyl, nitro or halogen.

Preferred as $R^1$ are $C_1$–$C_4$-alkylcarbonyl, benzyl, benzyl substituted on the phenyl, $C_1$–$C_6$-alkyloxycarbonyl and benzyloxycarbonyl. If the benzyloxycarbonyl radical is substituted by $OCH_3$, it preferably has one methoxy group in the p position. The $C_1$–$C_6$-alkyloxycarbonyl radical is particularly preferred.

Preferred $R^2$ radicals are OH and $C_1$–$C_4$-alkoxy.

Preferred $R^5$ radicals are $C_{1-6}$-alkyl and benzyl, in particular $C_{1-4}$-alkyl.

Compounds I have one asymmetric carbon atom, and compounds II have two asymmetric carbon atoms, in the 5-membered ring. Compounds of the formula II can be employed as racemates, mixtures of diastereomers, and as diastereomerically pure and enantiomerically pure compounds. Compounds I may therefore be obtained, depending on the stereochemical structure of the compounds II employed as precursors, and the reaction conditions, as racemates or in optically active form.

Compounds of the formula II can be prepared by methods disclosed in the literature (for example D. J. Abraham, M. Mokotoff, L. Sheh, J. E. Simmons, J. Med. Chem. 26(4), (1983) 549).

Elimination of the sulfonic acid residue, ie. of the $-O-SO_2-R^5$ group, from optically active compounds of the formula II takes place with racemization if $R^2$ is $C_1$–$C_4$-alkoxy or benzyloxy. This results in racemic esters of 3,4-dehydroproline, which provide access, by subsequent enzymatic racemate resolution, both to D- and to L-3,4-dehydroproline derivatives:

Process A:
(R5=CH$_3$, R2=OCH$_3$)

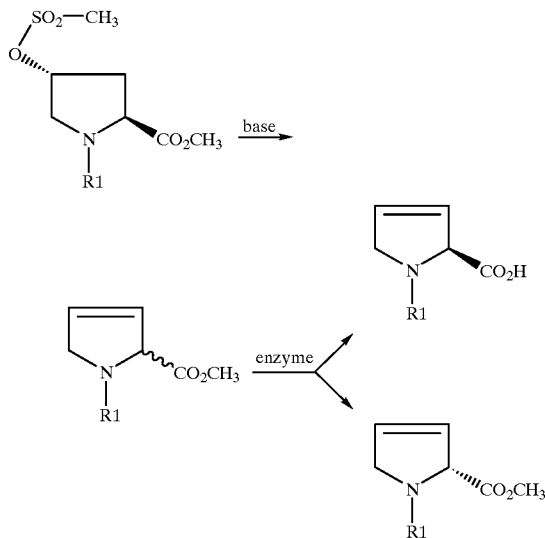

A particularly preferred embodiment of the process consists in using compounds of the formula II where R$^2$ is OH and the absolute configuration of the carboxylic acid residue is fixed, ie. corresponds either to the R or to the S configuration, to permit the corresponding carboxylic acids of the formula I to be obtained without racemization:

Process B:
(R5=CH$_3$, R2=OH)

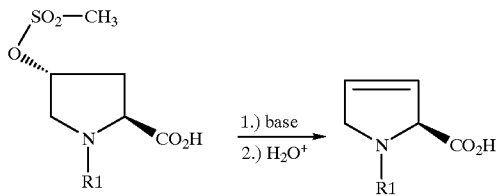

Aprotic solvents are suitable for elimination reactions A and B, in particular DMF, dioxane, THF, DME, DMSO, CH$_3$CN, it being possible for the solvent to contain small amounts of water or alcohol.

Depending on the process, 1.0–1.5 equivalents of base (process A) or 2.0–3.0 equivalents of base (process B) are employed, suitable bases being hydrides, amides and alcoholates of lithium, sodium, potassium, rubidium, cesium, calcium or magnesium, but preferably those of sodium and potassium. Sodium alcoholates are preferably employed as bases, suitable alcoholate residues therein being of primary, secondary and tertiary alcohols. It is also possible to employ diols, triols, ether alcohols of the tri-, di- or monoethylene glycol monoether type or amino alcohols. Those which may be preferably mentioned are: triethylene glycol monomethyl ether, diethylene glycol monomethyl ether or ethylene glycol monomethyl ether, dimethylaminoethanol or 2-[2-(dimethylamino)ethoxy]-ethanol.

Elimination of the sulfonate group takes place even at a temperature of −20° C. The reaction can in general be carried out from −20° C. to +100° C. It is preferably carried out at from −10° C. to 60° C. Elimination of the sulfonate group from the corresponding esters by process A takes place with racemization even at −20° C. on the a carbon atom of the 3,4-dehydroproline ester produced thereby.

Surprisingly, the process in the particularly preferred variant of process B can be carried out with precursors of the formula II where R$^2$ is OH, and the carboxylic acid residue has either the R or S configuration, almost without racemization. The bases preferably employed in this variant are hydrides, primary alcoholates, primary ether alcoholates or primary amino alcoholates. 2-Methoxyethanolate, 2-(2-methoxyethoxy)ethanolate or 2-[2-(dimethylamino)ethoxy] ethanolate are particularly preferably employed. From 2.0 to 2.5 equivalents of base are preferably employed per equivalent of precursor. The preferred temperature range for the reaction in process B is from −10° C. to +25° C.

The base used for the elimination can be introduced in solid form into the reaction mixture, but it can also be prepared in situ before the reaction. If, for example, the base used for the elimination is sodium 2-methoxyethanolate, this base can advantageously be prepared in situ by dropwise addition of the appropriate alcohol to a solution or suspension of a sodium salt of a stronger base such as sodium hydride, sodium tert-butoxide or sodium bis(trimethylsilyl) amide. The reaction can be carried out semibatchwise either by running the base solution into a dissolved precursor of the formula II or, preferably, running a solution of precursor II into the solution or suspension of base.

The reaction mixture can be worked up by distillation, extraction, crystallization, chromatography or a combination thereof.

The required enantiomer can be isolated from racemic 3,4-dehydroproline with either (+)- or (−)-tartaric acid (see J. W. Scott et al., Synthetic Communications 10 (1980) 529 and U.S. Pat. No. 4,111,951), or the racemate resolution can be carried out with optically active 1-(4-nitrophenyl) ethylamine after preparation of the Boc-protected amino acid (U.S. Pat. No. 4,066,658, J.-U. Kahl, T. Wieland, Liebigs Ann. Chem. 8, (1981) 1445).

N-protected 3,4-dehydroprolines prepared without racemization by preferred process B can advantageously be purified by crystallization as ammonium salts with achiral amines. It is possible in particular to obtain L-boc-3,4-dehydroproline in pure form as diethylammonium salt.

The invention therefore relates to compounds of the formula IV

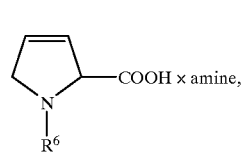

(IV)

where R$^6$ is an amino protective group and amine is a mono-, di- or trialkylamine where the alkyl radicals contain 1–4 carbon atoms and can be replaced by C$_{5-7}$-cycloalkyl radicals, and their optically active D and L forms. R$^6$ is preferably the boc protective group and "amine" is preferably diethylamine or dicyclohexylamine.

Esters obtained by process A can be very effectively partially cleaved using enzymes such as lipases, esterases and proteases, resulting in one antipode of the free acid, while the other antipode remains in the form of the ester.

A large number of enzymes can be employed as hydrolases in the said process. Proteases, esterases and, in particular, lipases are preferably used. Microbial lipases are particularly suitable lipases and can be isolated, for example, from yeasts or bacteria. Further particularly suitable hydrolases are the enzymes commercially obtainable from Novo Nordisk (Enzyme Toolbox), in particular the lipases SP 523, SP 524; SP 525, SP 526 and ®NOVOZYM 435 (*Candida antarctica*, lipase fraction B).

It is furthermore possible to employ the lipases "Chirazyme™ L1 to L8", which are commercially available from Boehringer Mannheim (L-1, *Burkholderia cepacia*, lipase; L-2, *Candida antarctica*, lipase fraction B; L-3, *Candida rugosa*, lipase; L-4, Pseudomonas sp., lipase; L-5, *Candida antarctica*, lipase fraction A; L-6, Psuedomonas sp., lipase; L-7, lipase, source not specified; and L-8, lipase, source not specified), advantageously in the process according to the invention.

Esterases such as pig liver esterase can also be employed.

The enzymes can be employed in native or in immobilized form.

The ester cleavage is carried out in a buffer at pH 6–8 and preferably at room temperature.

The novel process makes it possible to prepare compounds I in a very simple manner. It is particularly important for preparing dehydroproline derivatives which it has hitherto been possible to prepare only with difficulty and, in some cases, with poor yield.

Optically active N-protected 3-pyrroline-2-carboxylic acid derivatives are obtained particularly favorably by the novel process as free acid or in the form of an ester from which the free acid can be liberated, preferably enzymatically.

If optically active acid is prepared from the ester enzymatically, as a rule one antipode of the ester remains unchanged. The latter can be, for example, racemized with bases and subjected to the enzymatic cleavage again.

The advantage of the present invention is that it makes it possible for the first time to prepare 3,4-dehydroproline derivatives in sterically pure form simply and under mild and, at the same time, environmentally acceptable reaction conditions even on the industrial scale. It is surprising that elimination of the sulfonic acid residue can be carried out even at low temperatures.

The substances prepared by the novel process are of great interest. They are, for example, valuable intermediates for preparing low molecular weight peptide derivatives which are thrombin inhibitors (cf. WO 94/29336) and in which a proline residue is replaced by a dehydroproline residue. It has furthermore been found that 3,4-dehydroproline can be used to inhibit collagen synthesis (U.S. Pat. No. 4,066,658).

It is particularly advantageous for further processing that the crude product obtained by the process according to the invention can be reacted without further purification to prepare the next intermediates for the peptide derivatives which in turn can be purified very easily. These intermediates have the formula

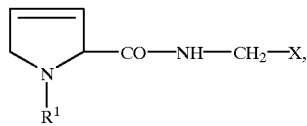

III where $R^1$ has the stated meaning, and X is

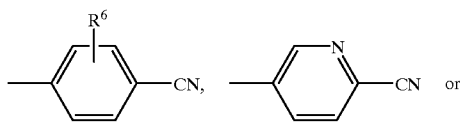

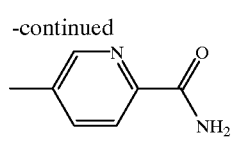

($R^6$=H, $CH_3$, $OCH_3$, OH or halogen).

They can be prepared from compounds I by activating the latter in the presence of a base such as triethylamine or diisopropylethylamine and a condensing agent such as PPA, pivaloyl chloride or dicyclohexylcarbodiimide/hydroxysuccinimide, and subsequently linking with $H_2N$—$CH_2$—X to give compounds of the formula III. The reaction is expediently carried out in a solvent such as dichloromethane, THF, dioxane, tert-butyl methyl ether, DME or acetonitrile at from −20 to +30°.

EXAMPLES

The following abbreviations are used in the examples:

Bns=Benzylsulfonyl
Boc=tert-Butyloxycarbonyl
DIPEA=Diisopropylethylamine
DME=Dimethoxyethane
DMF=Dimethylformamide
KOtBu=Potassium tert-butoxide
Ms=Methylsulfonyl
PPA=Propylphosphonic anhydride
Pro=Proline
Pyr=3,4-Dehydroproline
RT=Room temperature
THF=Tetrahydrofuran A. Preparation of the starting materials a) Boc-(L)-(4-MsO)-Pro-$OCH_3$ and Boc-(L)-(4-BnsO)-Pro-$OCH_3$:

(4R)-N-Boc-4-hydroxy-(L)-proline methyl ester was reacted with methylsulfonyl chloride to give (4R)-N-Boc-4-methyl-sulfonyloxy-(L)-proline methyl ester (D. J. Abraham, M. Mokotoff, L. Sheh, J. E. Simmons, J. Med. Chem. 26(4), (1983) 549). Similar to the reaction with Ms chloride, (4R)-N-Boc-4-benzylsulfonyloxy-(L)-proline methyl ester is obtained using benzylsulfony chloride in a yield of 76% after crystallization from ethanol. $^1$H-NMR (CDCl$_3$, δ in ppm): 7.40 and 7.28 (s, 5H, aromatic), 4.95 and 4.85 (m, 1H, O—CH), 4.40 (s, 2H, $SO_2$—$CH_2$), 4.4–4.25 (1H, N—CH), 3.72 and 3.71 (s, 3H, $CO_2CH_3$), 3.7–3.50 (2H, N—$CH_2$), 2.53–1.95 (2H, $CH_2$, 1.45 and 1.42 (s, 9H, Boc); (2 rotamers).

b) (4R)-N-Boc-(4-MsO)-Pro-OH:

186 g (575 mmol) of the methyl ester Boc-(L)-(4-MsO)-Pro-$OCH_3$ were hydrolyzed in 500 ml of dioxane and 1150 ml of 1N NaOE at 0° C. for 2.5 h. After extraction with ether, the aqueous phase was adjusted to pH 3 with 2N hydrochloric acid, and the product was extracted with ethyl acetate. Drying over $Na_2SO_4$ and stripping off the solvent completely resulted in 163 g (92%) of a yellowish oil which was 94% pure. The product slowly solidified;

$[\alpha]_D^{22}$=−50.5° (c=1.01; MeOH); after crystallization from diisopropyl ether $^1$H-NMR (CDCl$_3$, δ in ppm): ca. 9–8 (COOH), 5.35–5.20 (m, 1H, O—CH), 4.60–4.40 (1H, N—CH), 3.95–3.65 (2H, N-$CH_2$), 3.08 (s, 3H, $SO_2CH_3$), 2.85–2.25 (2H, $CH_2$), 1.50 and 1.40 (s, 9H, Boc); (2 rotamers)

B. Preparation of the final products

EXAMPLE 1

Preparation of Boc-(D/L)-Pyr-OCH$_3$:

a) 100 g (309 mmol) of Boc-(L)-(4-MsO)-Pro-OCH$_3$ were dissolved in 600 ml of dry DMF. At 0–5° C., a solution of 36.45 g (325 mmol) of KOtBu in 300 ml of dry DMF was added dropwise over the course of 1 h, and stirring was continued at 0–5° C. for 30 min and at RT for 2 h. The mixture was then poured into ice-water and extracted three times with ether/ethyl acetate 5:1, and the organic phase was again washed with water. After drying over Na$_2$SO$_4$, the solvent was completely stripped off at 35° C. 68 g of crude ester were obtained and were distilled at 100–102° C. under 1.7 mbar. The resulting colorless oil solidified (56% yield).

$^1$H-NMR (CDCl$_3$, δ in ppm): 6.05–5.95 (m, 1H, —CH=CH—), 5.80–5.67 (m, 1H, —CH=CH—), 5.05 and 4.98 (m, 1H, N—CH), 4.35–4.15 (m, 2H, N—CH$_2$), 3.75 and 3.74 (s, 3H, CO$_2$CH$_3$), 1.47 and 1.43 (s, 9H, Boc); (2 rotamers)

b) The same compound (Boc-(D/L)-Pyr-OCH$_3$) was also obtained from the benzylsulfonate Boc-(L)-(4-BnsO)-Pro-OCH$_3$. From 5 g (12.5 mmol) of said benzylsulfonate in 50 ml of dry DMF, which was added dropwise to a suspension of 0.5 g (12.5 mmol) of NaH in 10 ml of dry DMF at −10° C. and then stirred at RT overnight, there were obtained after workup similar to the elimination of the mesylate in a) 2.2 g of crude ester. The product was purified by column chromatography on silica gel (mobile phase: ethyl acetate/hexane 2:3). However, distillation is preferable because the chromophore is weak.

EXAMPLE 2

Preparation of Boc-(L)-Pyr-OH:

a) 50.0 g (161.6 mmol) of Boc-(L)-(4-MsO)-Pro-OH dissolved in 650 ml of DME (to which 25 mmol of water were added) were added dropwise in 45 min to 14.5 g of 55–65% NaH (about 364 mmol) in 400 ml of DME at room temperature, the temperature rising without additional cooling to about 30° C. The mixture was stirred at RT for a further 15 h and then at 50° C. for 1 h, subsequently poured into ice-water and washed three times with ether/ethyl acetate 2:1. The aqueous phase was acidified to pH 2 with 2N hydrochloric acid, and the product was extracted with ethyl acetate. Drying over Na$_2$SO$_4$ and stripping off the solvent completely resulted in 36 g of crude substance as yellowish oil which contained 70% of product. The product/precursor ratio was found to be 97:3 (HPLC: water/acetonitrile 8:2+0.1% TFA; Merck ®PUROSPHER RP-18e; detection at 210.4 nm) and the enantiomer ratio (L):(D) was 90:10. The proportions of enantiomers were detected on a chiral HPLC column as Boc-3,4-dehydroprolyl 3-picolylamide after coupling the acidic group with a 3-picolylamine derivative. Previous investigations have shown that the coupling itself takes place virtually without racemization.

A similar reaction but with 3 equivalents of NaH and stirring at RT for 4 h resulted in 65% of product (product:precursor=94:6; (L):(D)=96:4).

$^1$H-NMR (CDCl$_3$, δ in ppm) : 10.5–9.5 (COOH), 6.10–5.90 (1H, —CH=CH—), 5.88–5.70 (1H, —CH=CH—), 5.12–4.95 (1H, N—CH), 4.30–4.15 (2H, N=13 CH$_2$), 1.55–1.35 (9H, Boc); (2 rotamers)

By classical racemate resolution methods, Boc-3,4-dehydroproline and (+)-dehydroabietylamine were crystallized as corresponding ammonium salt from acetone and, without further recrystallization and after elimination of the amine, Boc-(L)-3,4-dehydroproline was isolated with a purity of 85% and an enantiomer ratio (L):(D) 96:4.

b) 46.2 g of sodium tert-pentoxide (398.5 mmol) were introduced into 150 ml of THF. Then, at 10° C., 32.9 g of 2-methoxyethanol (429.5 mmol) were added. A solution of 50 g of Boc-(L)-(4-MsO)-Pro-OH (159.4 mmol) in 100 ml of THF was then added dropwise in such a way that the internal temperature did not exceed 8–10° C. The mixture was stirred at 10° C. for a further 20 h after the end of the addition. Addition of 300 ml of ice-water at 5–10° C. was followed by one extraction with 50 ml of methyl tert-butyl ether and then acidification to pH 2 with hydrochloric acid. The crude product was extracted with methylene chloride and, after the solvent had been evaporated off, isolated as yellow oil. The weight was 40.9 g, of which 18 g was Boc-(L)-3,4-dehydroproline, determined by HPLC analysis calibrated with external standard (initial gradient water (0.1% H$_3$PO$_4$)/acetonitrile 70:30; column: Prodigy (ODS3) 100A; detection at 210 nm). The (L):(D) enantiomer ratio of 99:1 was likewise determined by HPLC analysis (hexane/isopropanol 8.75:1.25, 0.1% HCOOH; column: Chiracel OD; detection at 230 nm).

70 g of Boc-(L)-(4-MsO)-Pro-OH (224 mmol) were reacted under similar conditions. After extraction with methylene chloride, the crude product was transferred into 220 ml of methyl tert-butyl ether by distillative solvent exchange, and then the Boc-(L)-3,4-dehydroproline present therein was precipitated as diethylammonium salt by adding 16.5 g of diethylamine (224 mmol). 23.8 g of this salt were obtained. The (D) enantiomer was undetectable by the HPLC analytical methods indicated above in the product precipitated in this way.

$^1$H-NMR (DMSO, δ in ppm): 5.86–5.67 (2H, —CH=CH—), 4.6–4.5 (N—CH), 4.1–3.9 (N—CH$_2$), 2.88–2.7 (4H q, NCH$_2$CH$_3$), 1.45–1.25 (9H, Boc 2 rotamers), 1.2–1.05 (6H, NCH$_2$CH$_3$) [α]$_D^{22}$=−240.1° (C=1.08, MeOH) Melting point: 130–133° C.

c) 10.52 g of sodium bis(trimethylsilyl)amide (57.4 mmol) were introduced into 25 ml of THF and, after dropwise addition of 8.25 g of 2-[2-(dimethylamino)ethoxy] ethanol (62 mmol) in 15 ml of THF over the course of 15 min with cooling, stirred at RT for 30 min. Then, at −5° C., 7.1 g of Boc-(L)-(4-MsO)-Pro-OH (23.0 mmol) dissolved in 15 ml of THF were added dropwise over the course of 20 min, and the mixture was stirred at −5° C. for 1 h, at 0° C. for 2 h and at RT overnight. It was then poured onto 125 g of ice-water and extracted four times with methyl tert-butyl ether, and the aqueous phase was acidified to pH 2.2 with 60 ml of 10% strength citric acid and stirred at RT overnight. After the reaction solution had been extracted with methyl tert-butyl ether three times, the collected organic phases were washed successively with water, saturated brine and water, dried over magnesium sulfate and concentrated under reduced pressure. 4.1 g of Boc-(L)-3,4-dehydroproline were obtained as crude product which was then dissolved in 20 ml of methyl tert-butyl ether, and a solution of 1.35 g of diethylamine (18.52 mmol) in 10 ml of methyl tert-butyl ether was added dropwise. Petroleum ether was added to complete precipitation of the salt. The product was filtered off with suction and dried to afford 4.0 g of Boc-(L)-3,4-dehydroproline. A second batch of 0.3 g of crystals was also obtained from the mother liquor, which means that the total yield of required product was 66%.

EXAMPLE 3

Preparation of Boc-(D,L)-Pyr-OH:

13 g of isopropanol (215 mmol) were added dropwise to 8 g of 60% NaH (200 mmol) in 150 ml of DME with cooling. After evolution of $H_2$ had subsided, at 0° C. a solution of 25 g of Boc-(L)-(4-MsO)-Pro-OH (80 mmol) in 100 ml of DME was added. 1 h at 0° C. was followed by warming at 20° C. for 20 h, and then addition of 150 ml of water. One extraction with methyl tert-butyl ether was followed by acidification to pH 2 with hydrochloric acid and extraction with methylene chloride. The weight of product was 17 g. The (L):(D) enantiomer ratio was determined by HPLC analysis (hexane/isopropanol 8.75:1.25, 0.1% HCOOR; column: Chiracel OD; detection at 230 nm) as 57:43.

EXAMPLE 4

Enzymatic cleavage of Boc-(D/L)-Pyr-OCH$_3$ to Boc-(L)-Pyr-OH:

5.68 g (25 mmol) of Boc-(D/L)-Pyr-OCH$_3$ in 100 ml of phosphate buffer (pH 7.0) and 15 ml of THF were shaken with 3.12 g of ®NOVOZYM 435 at RT for 24 h. During this, the pH was adjusted back to the initial value by adding 1N NaOH. The progress of the reaction was observed from the consumption of sodium hydroxide solution. The solid was filtered off, and the filtrate was adjusted to pH 10 with 1N NaOH. The unreacted anti-pode Boc-(D)-Pyr-OCH$_3$ was extracted with ethyl acetate/ether 1:1. The aqueous phase was adjusted to pH 1 with 1N hydrochloric acid, and the product Boc-(L)-Pyr-OH was extracted three times with ethyl acetate. 2.14 g of product were obtained and were crystallized from toluene/hexane or ether/hexane. After crystallization, the product had an optical rotation of $[\alpha]_D^{22}=-273.8°$ (c=1.03; methanol). (Lit.: $[\alpha]_D^{25}=-272°$ (c=1.0; methanol) J.-U. Kahl, T. Wieland, Liebigs Ann. Chem. 8, (1981) 1445).

USE EXAMPLE 1

Preparation of H-(L)-Pyr (6-carboxamido)-3-picolylamide dihydrochloride:

5.3 ml (30.3 mmol) of DIPEA were added dropwise to 1.5 g of crude Boc-Pyr-OH from Example 2 in 30 ml of dichloromethane at −10° C. and, after 5 min, 1.58 g (7.0 mmol) of (6-carboxamido)-3-picolylamide dihydrochloride were added and, after a further 5 min, 5.7 ml (7.9 mmol) of PPA (50% strength solution in ethyl acetate) in 5 ml of dichloromethane were added. The reaction mixture was allowed to warm from −10° C. to 0° C. over 1 h and was then diluted with dichloromethane and washed successively with saturated NaHCO$_3$ solution, 5% strength citric acid and saturated brine. Drying of the organic phase over Na$_2$SO$_4$ and stripping off the solvent completely resulted in 1.8 g of crude Boc-(L)-Pyr (6-carboxamido)-3-picolylamide which was stirred in 30 ml of 0.9 molar isopropanolic HCL at 50° C. for 50 min. The precipitate which was produced during this was removed on a suction filter, dissolved in a little methanol, precipitated with isopropanol and again removed. Drying at 45° C. under reduced pressure resulted in 2.0 g of H-(L)-Pyr (6-carboxamido)-3-picolylamide dihydrochloride as white powder (purity 95%); (L):(D)>99:1.

$^1$H-NMR (DMSO-d$^6$, δ ppm) : 10.9 and 8.9 (each 1H, —NH$_2$—⊕), 9.77 (t, 1H, CO—NH), 8.60, 8.10 and 8.00 (each 1H, aromatic H), 8.25 and 7.75 (each 1H, CO—NH$_2$), 6.03 (s, 2H, —CH=CH—), 5.10 (1H, N—CH—CO) 4.47 (d, 2H, CH$_2$) 4.00 (2H, CH$_2$)

USE EXAMPLE 2

Preparation of H-(L)-Pyr 4-CN-benzylamide hydrochloride:

10.0 g of crude Boc-Pyr-OH were reacted with 6.2 g of p-cyanobenzylamine as in Use Example 1. Workup resulted in 14.7 g of crude Boc-(L)-Pyr 4-CN-benzylamide which was stirred in 230 ml of 1 molar isopropanolic HCl at 50° C. for 2 h. After the solution had cooled to RT, the substance began slowly to precipitate. The solid was removed on a suction filter. 3.7 g of H-(L)-Pyr 4-CN-benzylamide hydrochloride were obtained as a white powder (purity 96%; (L):(D)>99:1). $^1$H-NMR (DMSO-d$^6$, δ in ppm) : 10.9 and 8.9 (each 1H, —NH$_2$—⊕), 7.82 and 7.47 (each 2H, aromatic H), 6.02 (s, 2H, —CH=CH—), 5.10 (1H, N—CH—CO) 4.45 (d, 2H, CH$_2$) 4.02 (2H, CH$_2$)

We claim:

1. A process for preparing 3-pyrroline-2-carboxylic acid derivatives of the formula I

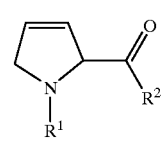

(I)

where

R$^1$ is H, C$_1$–C$_6$-alkyl, benzyl, benzyl substituted on the phenyl, allyloxycarbonyl, C$_1$–C$_6$-alkyloxycarbonyl, benzyloxycarbonyl where the benzyl residue can be substituted by OCH$_3$ radicals, or C$_1$–C$_6$-alkylcarbonyl or R$^1$ is a residue of an amino acid which is linked via the C terminus and may be alkylated or acylated on the nitrogen, and R$^2$ is OH, C$_1$–C$_6$-alkyloxy, benzyloxy or N R$^3$4$^2$, where R$^3$ and R$^4$ are independently of one another, H, C$_1$–C$_6$-alkyl, benzyl, phenyl or pyridyl, the aromatic systems in R$^3$ and r$^4$ being optionally substituted by up to three identical or different substituents selected from the group consisting of methyl, methoxy, hydroxyl, cyano or halogen, which comprises eliminating the sulfonic acid radical with the aid of a base selected from the group consisting of hydrides, amides and alcoholates of lithium, sodium, potassium, rubidium, cesium, calcium or magnesium from a compound of the formula II

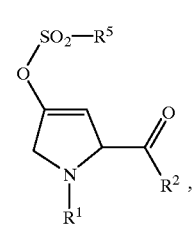

(II)

where R$^1$ and R$^2$ have the meanings described above, and R$^5$ is C$_1$–C$_6$-alkyl, benzyl, trifluoromethyl, naphthyl or phenyl which may be unsubstituted or substituted by radicals from the group consisting of methyl, nitro or halogen.

2. A process as claimed in claim 1 for preparing an optically active 3-pyrroline-2-carboxylic acid, wherein the sulfonic acid radical is eliminated with the aid of a base selected from the group consisting of hydrides, amides and alcoholates of lithium, sodium, potassium, rubidium, cesium, calcium or magnesium from a compound of the formula II, where $R^1$ and $R^5$ have the meanings described above, and $R^2$ is $C_1$–$C_4$-alkyloxy or benzyloxy, and the optically active free acids are liberated enzymatically from the obtained racemic ester in the form of ammonium salts.

3. A process as claimed in claim 1 for preparing an optically active 3-pyrroline-2-carboxylic acid, wherein the sulfonic acid radical is eliminated with the aid of a base selected from the group consisting of hydrides, amides and alcoholates of lithium, sodium, potassium, rubidium, cesium, calcium or magnesium from a compound of the formula II where the carboxylic acid residue has either the (R) or the (S) configuration, $R^1$ and $R^5$ have the abovementioned meanings, and $R^2$ is OH, and the obtained products are optionally converted into ammonium salts for purification and isolation.

4. A process as claimed in claim 1 for preparing 3-pyrroline-2-carboxylic acid derivatives and subsequently converting the obtained 3-pyrroline-2-carboxylic acid derivatives to compounds of the formula II

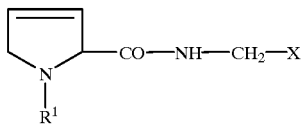

III where $R^1$ has the stated meaning, X is

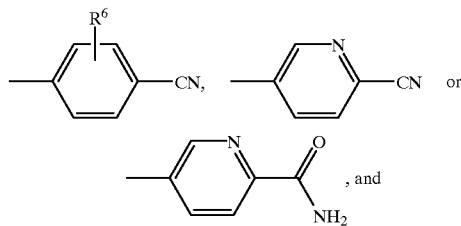

$R^6$ is H, CH3, OCH3, OH or halogen.

5. A compound of the formula IV

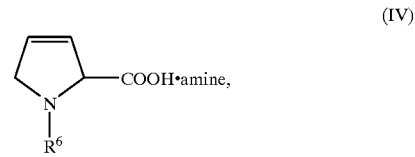

(IV)

where $R^1$ is an amino protective group selected from allyloxycarbonyl, $C_1$–$C_6$-alkyloxycarbonyl, benzyloxycarbonyl or $C_1$–$C_4$-alkylcarbonyl, and amine is a mono-, di- or trialkylamine where the alkyl radicals contain 1–4 carbon atoms and may be replaced by $C_{5-7}$-cycloalkyl radicals.

6. A compound of the formula IV as claimed in claim 5, where $R^1$ is the Boc protective group and the amine is diethylamine or dicyclohexylamine.

7. A compound as claimed in claim 5 in the D form.

8. A compound as claimed in claim 5 in the L form.

* * * * *